United States Patent [19]

Erdman et al.

[11] Patent Number: 4,676,784
[45] Date of Patent: Jun. 30, 1987

[54] STABLE DISPOSABLE ABSORBENT STRUCTURE

[75] Inventors: Edward P. Erdman, Cranbury; Heinz A. Pieniak, North Brunswick, both of N.J.

[73] Assignee: Personal Products Company, Milltown, N.J.

[21] Appl. No.: 605,964

[22] Filed: May 1, 1984

[51] Int. Cl.$^4$ ............................................. A61F 13/20
[52] U.S. Cl. ..................................... 604/368; 604/369
[58] Field of Search .............. 604/369, 372, 378, 379, 604/365, 374, 366, 375, 367, 368, 385, 380

[56] References Cited

U.S. PATENT DOCUMENTS

| | | | |
|---|---|---|---|
| Re. 26,151 | 1/1967 | Duncan et al. | 604/379 |
| 3,592,194 | 7/1971 | Duncan | 604/379 |
| 4,145,464 | 3/1979 | McConnell et al. | 604/378 |
| 4,323,069 | 4/1982 | Ahr | 604/372 |
| 4,327,728 | 5/1982 | Elias | 604/368 |
| 4,333,463 | 6/1982 | Holtman | 604/368 |
| 4,381,783 | 5/1983 | Elias | 604/378 |
| 4,500,315 | 2/1985 | Pieniak et al. | 604/379 |

Primary Examiner—John D. Yasko
Attorney, Agent, or Firm—Robert L. Minier

[57] ABSTRACT

An absorbent product is provided which is disposable, light weight, stable and potentially thin. It is comprised of a superstructure of resilient fibers in combination with superabsorbent, which combination is provided with apertures. The apertures and at least one side of the superstructure are covered with hydrophilic material.

12 Claims, 6 Drawing Figures

STABLE DISPOSABLE ABSORBENT STRUCTURE

BACKGROUND OF THE INVENTION

The present invention relates to new and improved stable disposable absorbent structures and more particularly, to diapers and sanitary napkins containing the new absorbent structures as the absorbent core of the product.

Disposable absorbent products have been known for some time including such products as disposable diapers, sanitary napkins, wound dressings, bandages, incontinent pads and the like. These products incorporate an absorbent batt which is used to absorb and hold or contain body fluids. Initially in many of these products, especially diapers and sanitary napkins, the absorbent batt comprised what is termed "wadding" or plies of tissue. The wadding was disposed between a liquid-impermeable backing and a liquid-permeable facing and the plies of tissue were used to absorb and hopefully contain the liquid within the product. A diaper which utilizes such an absorbent batt is disclosed in U.S. Pat. No. Re. 26,151.

The wadding type of product was replaced for the most part by an improved absorbent batt which comprises what is termed "fluffed wood pulp fibers". This absorbent batt comprises a layer of individualized wood pulp fibers with the layer having substantial thickness. A diaper which incorporates such a fluffed wood pulp absorbent batt is described in U.S. Pat. No. 2,788,003. This diaper had improved absorbent capacity and somewhat better containment ment than a diaper using a wadding layer. Also the fluffed wood pulp layer is quite soft, flexible and conformable and, hence, produces an improved diaper over diapers using wadding as the absorbent layer.

Though the fluffed wood pulp absorbent batts have improved capacity, the efficiency with which the capacity is used in a diaper or sanitary napkin is poor. One of the reasons for this is that the fluffed wood pulp absorbent batt tends to break apart upon flexing. Furthermore, once the absorbent batt has accepted a substantial amount of liquid, the cellulosic fibers tend to collapse, sometimes causing liquid to be squeezed from the product and to leak. Another reason is that the fluid to be absorbed is generally deposited in a localized area within the absorbent batt and the ability of the fluid to move along the plane of the batt is poor. The fluid tends to follow a radial wicking path and, consequently, moves to the closest edge of the batt where it generally is no longer contained and the product leaks. The only way in which the capacity can be increased is to add more pulp thus compounding the problems already present and thickening the product making it more bulky.

In answer to some of the problems, U.S. Pat. No. 3,017,304 incorporated in the absorbent batt a densified paper-like layer. This paper-like layer acts as a wick i.e., liquid which is placed on the layer tends to move rapidly along the plane of the layer. When incorporated in combination with fluffed wood pulp fiber, the resultant product uses the absorbent capacity of the fluffed wood pulp much more efficiently. However, the paper-like densified layer is subject to fracture and though it stabilizes the absorbent batt to some degree, fracturing occurs too frequently. Diapers which incorporate this paper-like layer combined with fluffed wood pulp are disclosed and described in U.S. Pat. Nos. 3,612,055 and 3,938,522. This concept of combining wicking ability or a capillary skin layer with fluffed wood pulp fibers has gained wide acceptance in many absorbent products, including disposable diapers and sanitary napkins. Even though these products make much greater use of the capacity of the absorbent batt, they still do not totally contain the absorbed liquid. It is probable that these products will leak before the full capacity of the batt is used for the absorption or, at the very least, before the entire liquid void by the user is absorbed. This is especially true when pressure is placed on the batt while wet. For example, a baby sitting down on a previously wetted diaper will very often cause the batt to leak.

A number of years ago in answer to increasing capacity of absorbent products "superabsorbent materials" i.e., materials which will absorb many times their weight of liquid, were developed. Since the development of such materials, attempts to incorporate them in absorbent products, such as diapers, to enhance the absorption performance of these products have been made. Theoretically, a minimum amount of superabsorbent incorporated in a product would make that product perform as well or better than the prior art products. Perhaps one of the first products to incorporate such a superabsorbent material in a disposable diaper is disclosed in U.S. Pat. No. 3,670,731. This patent discloses an absorbent dressing comprising an absorbent layer sandwiched between a permeable facing and an impermeable backing sheet. The absorbent layer contains water-insoluble cross-linked hydrocolloid polymer as the superabsorbent material.

Even though superabsorbent materials have been available for some time, they have not gained wide acceptance in absorbent products such as disposable diapers, sanitary napkins, incontinent pads and the like. A primary reason for this lack of acceptance of superabsorbents is failure to develop a product capable of economically utilizing the highly increased absorptive capacity of the superabsorbent material. In order to economically utilize a superabsorbent, the liquid being absorbed must be readily accepted and placed in contact with the superabsorbent material. Furthermore, as the superabsorbent material absorbs liquid it must be allowed to swell. If the superabsorbent is prevented from swelling, it will cease absorbing liquid. Hence, if the superabsorbent material is to function in absorbent products such as diapers, sanitary napkins and incontinent pads, wherein the liquid to be absorbed is placed in a small void area, the structure of the absorbent layer containing superabsorbent materials must have certain characteristics. Over the years a number of techniques have been disclosed in an attempt to provide structures which make efficient use of the superabsorbent material. Such products are disclosed in U.S. Pat. Nos. 4,103,062, 4,102,340 and 4,235,237. In addition, methods for incorporating superabsorbents into suitable layers or suitable configurations which can be placed in an absorbent product are disclosed in U.S. Pat. Nos. 4,186,165, 4,340,057 and 4,364,992. To date, none of these products has met with any substantial commercial success.

The present invention provides a new and improved absorbent product which is dimensionally stable when in use and which possesses an absorbent core containing superabsorbent material, cellulosic fibers and resilient fibers. The new absorbent product will contain absorbed liquid even when pressure is placed upon the product during use.

SUMMARY OF THE INVENTION

The present invention provides an absorbent product which is disposable, light weight, and potentially thin and is stable and which comprises a substantially stable, flexible, absorbent fibrous superstructure containing at least about 10% by weight of superabsorbent. The superstructure has openings substantially filled and is covered on at least one side thereof with a hydrophilic porous material which provides a capillary pressure to absorbed liquid that is higher than that provided by the superstructure. Preferably, the fibrous superstructure is a web of resilient fibers which has an initial dry bulk of at least about 10 cc per gram before being covered by the hydrophilic material. The openings in the superstructure may be apertures or may be created by placing strips of the web in a configuration which provides channels which are covered over with the hydrophilic material.

The hydrophilic material is a porous material and is selected from the group consisting of open-cell cellulose foam, cellulosic fibers, peat moss, acrylic fibers, or the like and mixtures thereof. The hydrophilic material is at least lightly compacted after being placed on the superstructure.

The fibrous superstructure preferably is comprised of substantially resilient synthetic fibers in the form generally of a non-woven web. The fibers are both wet and dry resilient. The superabsorbent material used to provide the superabsorbent portion may be of a wide range of particle size and is distributed in any one of a number of ways e.g., as a layer or film or as individual particles or globules or as part of the superstructure during formation of the superstructure.

The absorbent product is suitable for use in a disposable diaper, a sanitary napkin, an incontinent pad, a wound dressing, bandages and the like.

DETAILED DESCRIPTION OF THE INVENTION

Figure 1:
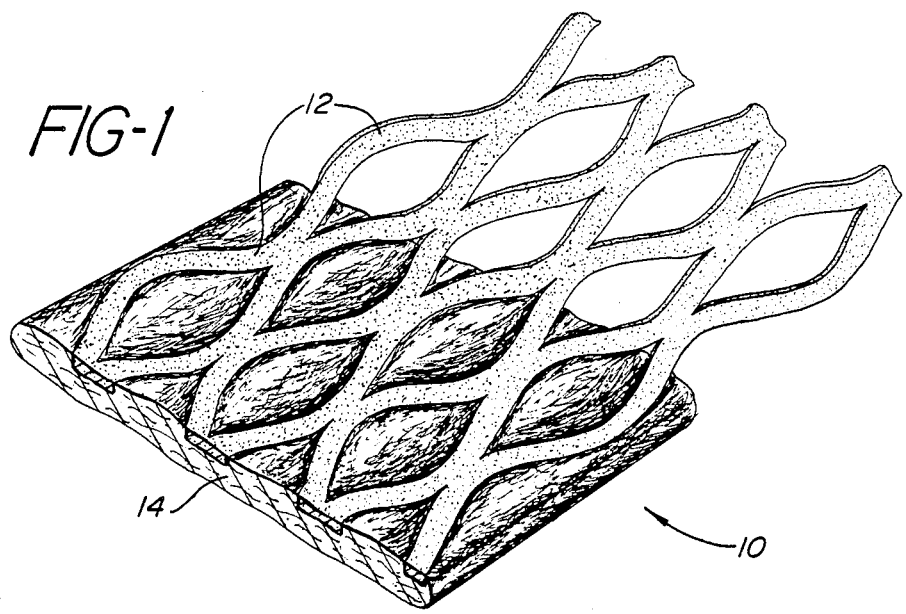
FIG. 1 is a perspective view of one embodiment of the present invention.

FIG. 1 represents a perspective view of an absorbent product 10 of the present invention. The absorbent product 10 has a diamond-shaped grid-like work of a fibrous web 12 which web contains at least about 10% by weight superabsorbent material. Cellulosic fibers 14 are placed in the openings to fill the holes or apertures of the grid and over one side of the grid and lightly compacted to provide a layer of hydrophilic fibers which accepts and wicks liquid.

Figure 2:
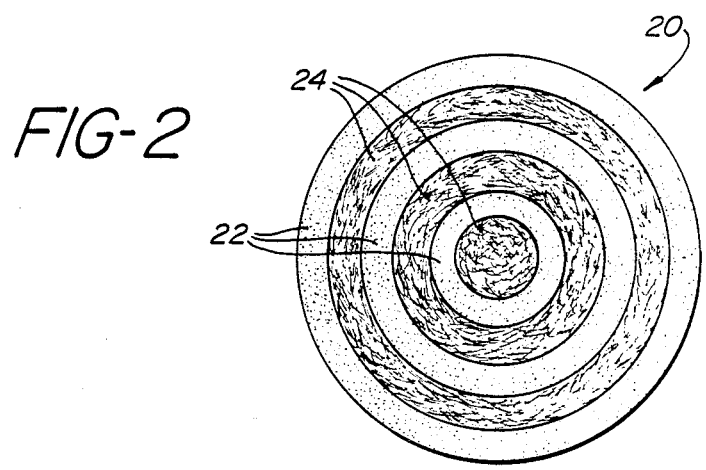
FIG. 2 is a perspective view of another embodiment of the present invention.

FIG. 2 depicts a plan view of another configuration of the absorbent product 20 of the present invention. In this configuration the fibrous web 22 containing superabsorbent is in diminishing circles in size, such that the circular web strips fit one within another leaving openings in between. The circular openings are filled with the loosely compacted cellulosic fibers 24 and a layer of the cellulosic fibers covers one side of the product.

Figure 3:
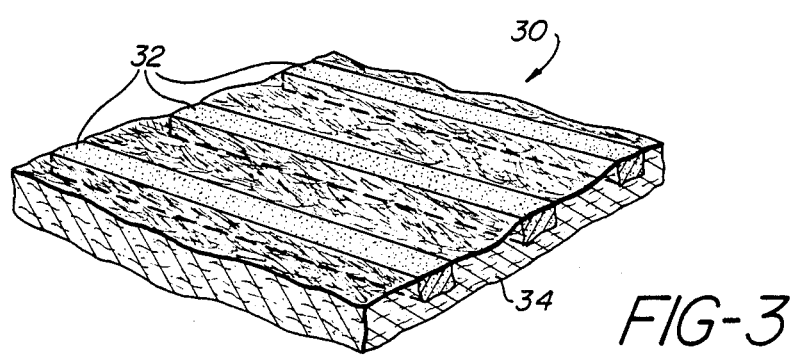
FIG. 3 is perspective view of a further embodiment of the present invention.

FIG. 3 is a perspective view of still another embodiment illustrating the absorbent product 30 of the present invention. The absorbent product 30 is comprised of fibrous web strips 32 placed apart from one another with loosely compacted cellulosic fibers 34 substantially surrounding the fibrous web strips and covering them. As before, the fibrous web strips contain superabsorbent material.

Figure 4:
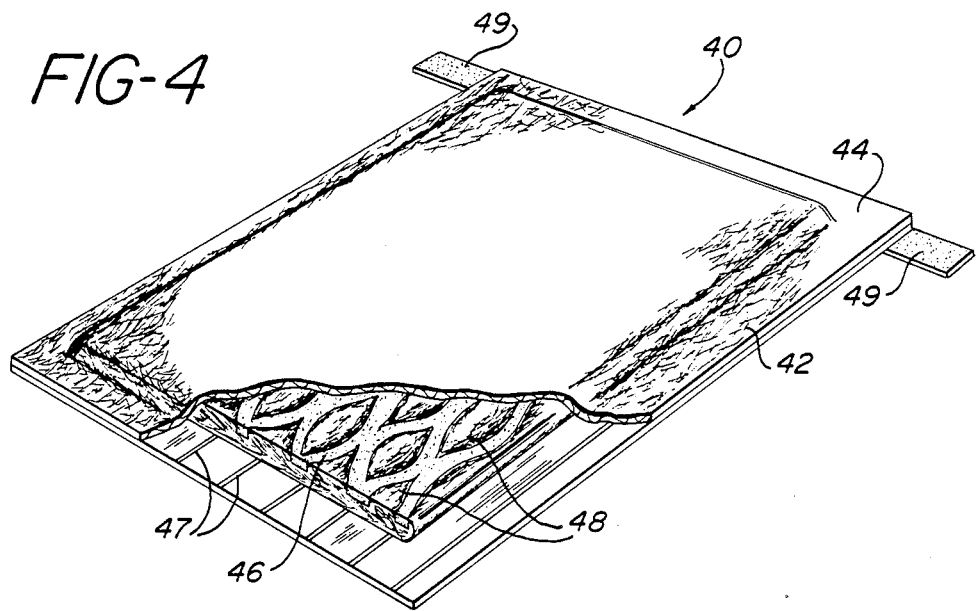
FIG. 4 is a perspective view of a diaper utilizing one embodiment of the present invention.

FIG. 4 is a perspective view of a diaper utilizing the absorbent product of the present invention. A portion of the diaper is broken away to clearly illustrate the construction of the product. The diaper 40 has a moisture-impermeable backing 42 generally in the form of a polyethylene film. A liquid-permeable facing 44 covers the product and is laminated in marginal portions to the liquid-impermeable backing 42. A suitable material for the liquid-permeable facing is a non-woven fabric such as a polyester fabric. The absorbent structure sandwiched between the facing and the backing is comprised of an apertured fibrous layer 46 containing superabsorbent material and loosely compacted cellulosic fibers 48 substantially filling the apertures of the fibrous web 46 and forming a layer beneath the web. The absorbent structure is smaller in size than the facing or the backing of the diaper. This permits lamination of the facing and the backing to each other to provide a unitary product. The absorbent structure is adhered to the backing 42, and the facing 44 and the backing 42 are laminated in the margins by use of glue lines 47. At one end of the diaper product tape tabs 49 ar provided to secure the diaper product about the waist of the wearer.

Figure 5:
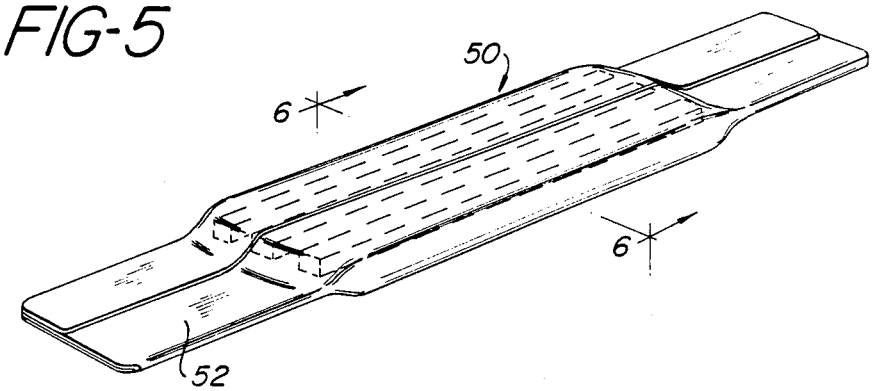
FIG. 5 is a perspective view of a sanitary napkin using another embodiment of the present invention.
Figure 6:
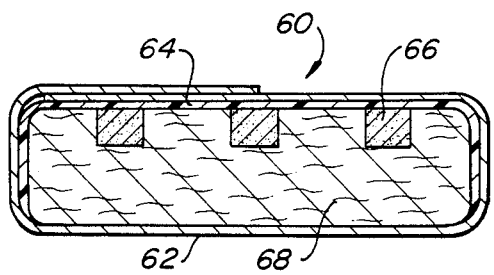
FIG. 6 is a cross-sectional view through lines 6—6 of FIG. 5.

FIG. 5 is a perspective view of a sanitary napkin 50 having a liquid-permeable overwrap 52. The product is shown in better detail in FIG. 6 is which a cross-sectional view taken along lines 6—6 of FIG. 5. In FIG. 6, the cross-section 60 shows the liquid permeable overwrap 62 as well as a liquid-impermeable film 64 encompassing the bottom and side edges of the sanitary napkin. The presence of the liquid-impermeable film 64 prevents leakage of liquid from the product when in use. Strips of the fibrous web 66 containing superabsorbent are provided separately and loosely compacted cellulosic fibers 68 substantially surround the strips of fibrous web 66.

These and other products such as incontinent pads, wound dressings, wipes and the like may be made from the absorbent product depicted in FIGS. 1, 2 and 3.

The preferred fibrous superstructure containing openings is generally of substantially high-loft and, upon dry compression followed by release, has a tendency to return substantially to its original thickness. For instance, fibrous webs formed from synthetic fibers such as polyethylene, polypropylene, polyester, nylon (polyamide fibers), bi-component fibers, mixtures thereof and the like, are particularly suitable. However, cellulosic fibers such as rayon may be used. Generally the fibers are carded or air laid to form a web which is then stabilized if needed. Stabilization may be achieved by heat-through bonding, adhesive bonding, point embossing with heat or adhesive or both and the like. The stabilizing process is selected according to the fibers used and the process used to form the web. Other suitable procedures for forming a web include wet-laying, spun bonding, laying of melt-blown fibers and other known techniques. The fibrous web preferably has a dry bulk of at least about 10 cc per gram and a weight less than about 4 oz. per sq. yd. (about 150 gms/sq.m.)

In one embodiment a blend of staple polyester fibers with a minor portion of fusible fibers, such as lower-melt polyester fibers, is carded to form a web. The web is subsequently lightly bonded by passing hot air through the fibers making the fusible fibers tacky so as to stick to each other and the staple fibers to provide the desired degree of integrity to the web structure.

The superabsorbent material present either on the fibers of the web or otherwise associated with the web is generally a water-swellable, water-insoluble polymeric substance capable of absorbing water in an amount which is at least ten times the weight of the substance in its dry form.

The superabsorbent is in the form of fibers, spheres, particles, bits of film, globules, webs, film, uniform coating, coated fibers or the like, or may be applied in the form of a liquid monomer solution which is subsequently polymerized. The superabsorbent prepared by polymerization of a monomer solution placed on fibers in a web is most frequently in the form of globules and bits of a film-like particles in the web structure.

One type of superabsorbent material provides particles or fibers which may be described chemically as having a backbone of natural or synthetic polymers with hydrophilic groups or polymers containing hydrophilic groups being chemically bonded to the backbone or an intimate mixture therewith. Included in this class of materials are such modified natural and regenerated polymers as polysaccharides, including for example, cellulose and starch and regenerated cellulose which are modified by being carboxyalkylated, phosphonoalkylated, sulfoalkylated, or phosphorylated to render them highly hydrophilic. Such modified polymers may also be cross-linked to improve their water-insolubility.

These same polysaccharides may also serve, for example, as the backbone on to which other polymer moieties may be bonded by graft copolymerization techniques. Such grafted polysaccharides and their method of manufacture are described in U.S. Pat. No. 4,105,033 to Chatterjee et al. and may be described as polysaccharide chains having grafted thereon a hydrophilic chain of the general formula:

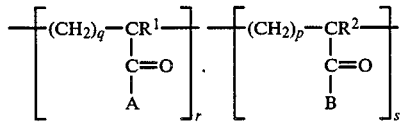

wherein A and B are selected from the group consisting of —OR$^3$, —O(alkali metal), —OHNH$_3$, —NH$_2$, wherein R$^1$, R$^2$, and R$^3$ are selected from the group consisting of hydrogen and alkylene having 1 to 4 or more carbon atoms wherein r is an integer having a value of 0 to about 5000 or more, s is an integer having a value of 0 to about 5000 or more, r plus s is at least 500, p is an integer having a value of 0 or 1, and q is an integer having a value of 1 to 4. The preferred hydrophilic chains are hydrolyzed polyacrylonitrile chains and copolymers of polyacrylamide and polysodium acrylate.

In addition to the modified natural and regenerated polymers, the hydrocolloid component may comprise wholly synthetic hydrophilic particles. Examples of those now known in the art are polyacrylonitrile fibers which may be modified by grafting moieties thereon such as polyvinylalcohol chains, polyvinyl alcohol itself, hydrophilic polyurethane, poly(alkyl phosphonates), partially hydrolyzed polyacrylamides (e.g., poly(N-N-dimethylacrylamide), sulfonated polystyrene, or a class of poly(alkyleneoxide). These highly hydrophilic synthetic polymers may be modified by other chemical treatments such as cross-linking or hydrolysis. Further examples known in the art are the non-ionic polymers such as polyoxyethylene, polyoxypropylene, and mixtures thereof which have been suitably cross-linked, either chemically or by irradiation. Still another more recent type is a derivative of isobutylenemalic and acrylate monomers, such as sodium, potassium, ammonium, (or a combination of cations), acrylate, may be placed on the absorbing layer by spraying or otherwise placing a solution thereon, followed by polymerization and cross-linking, for example, by irradiation.

In addition, naturally occurring materials such as gums may be used. Examples of such suitable gums include guar gums, acacia gums, locust bean gums and the like.

The superabsorbent is combined with the superstructure in such a manner as to remain substantially in the same position or region even though the superstructure may be moved about during manufacturing, packaging, or use. The superabsorbent is present in an amount from about 20% to about 90% by weight of the combined superstructure and superabsorbent, thus the superstructure is present in an amount from about 10% to about 80% by weight.

If the superabsorbent material is a powder, it may be sprinkled onto the fibrous superstructure web in dry form or may be moistened so as to assist in adhering the superabsorbent to the web fibers. If the superabsorbent is in granular form, it is desirable to slightly moisten the superabsorbent before placing it in contact with the web. The superabsorbent generally will be in the form of particles or fibers or globules or the like which may range in size from about 0.0005 mm in diameter to globules that are continuous along fibers for a distance of several inches.

Another method of placing superabsorbent in a fibrous web is by spraying a monomer solution on the web or perhaps even saturating the web with a monomer solution followed by polymerization of the monomer and cross linking. One typical way to polymerize the monomer is by use of irradiation which also assists in cross linking. It is desirable to place a superabsorbent somewhat evenly throughout the fibrous web. Any superabsorbent which absorbs large amounts of liquids is suitable for use in the absorbent product of the present invention.

As heretofore mentioned in order for the fibrous superstructure to provide the most desired medium for receiving and holding liquid, it is preferred that it be a fibrous web with a dry bulk of at least about 10 cc per gram and a weight less than about 4 oz. per sq. yd. The dry bulk is the area times thickness of the web under a load of 0.01 psi calculated in cubic centimeters. This value is divided by the weight in grams in order to provide the measurement in cubic centimeters per gram.

After application of the superabsorbent material, the fibrous web may be compressed to reduce the thickness of the web by at least about half of its original thickness. Generally the fibrous web is compressed in the presence of about 10% moisture so that the web remains compressed after the release of pressure. The presence of the moisture tends to render the superabsorbent material tacky, thus assisting in retention of the compressed form of the web.

The compressed web is then cut or formed into the shape desired. Although the web may have been preformed in the desired shape, it is quite likely that the shaping of the web will take place after formation of the web and placement of the superabsorbent material on the web. Any scrap material resulting from the shaping of the web can subsequently be ground and added to absorbent products providing an enhancement of the absorption capacity of the product.

The provision of openings in the fibrous web is accomplished in any number of ways. Perhaps the most economical way is to provide staggered parallel longitudinal slits in the web followed by transverse stretching of the web to open the slits. The resulting openings are of a diamond shape. The apertures can be of any shape and can be formed by the initial means of casting of the web, or by cutting out or by cutting into strips. Preferably, the aperture has a cross-direction of at least ¼ inch up to several inches. The apertures can be provided by slits cut in a cross-direction. For example, the slits are placed in staggered parallel rows substantially across the product and perhaps for a diaper product the slits and resulting apertures are only in the central portion of the product.

The apertured web is ready for assembly in a product, such as a disposable diaper or a sanitary napkin. In one embodiment, the apertured web is placed on a foraminous surface and wood pulp fibers are cast and drawn into the apertures by vacuum and in a layer to cover the apertures.

Alternatively, a layer of wood pulp fibers are placed on a polyethylene backing sheet substantially in a layer and the apertured web is laid on the wood pulp fiber layer. The wood pulp fibers may not substantially fill the apertures but the layer of wood pulp fibers assists in wicking liquid and the fibrous layer containing superabsorbent absorbs the liquid. The apertures in the fibrous layer readily accept liquid so that if the wicking layer is on the side away from the liquid void zone, the product still readily accepts liquid.

It may be desirable to add a specific wicking layer to the absorbent product of the present invention. Effective wicking layers include tissue, compressed wood pulp fibers such as those described in U.S. Pat. No. 3,017,304, peat moss, acrylic fibers and the like. The wicking layers provide a still higher capillary pressure for any absorbed liquid and hence tend to transport the liquid to other regions of the product.

In a diaper of the present invention, a stabilized nonwoven web of polyester fibers having a dry weight basis of about 2 oz./sq. yd. and containing 800% by weight superabsorbent is provided in grid form wherein each aperture is approximately one square inch in area. The grid is laid on a tissue on a foraminous surface. Wood pulp fibers are cast and drawn by vacuum into the apertures. The facing and backing are then laminated in margins extending beyond the apertured web to form a diaper.

Alternatively, a grid is placed on a facing and wood pulp fibers are cast in a layer over the grid, filling the apertures and providing a thin layer of its fibers. The surface of the wood pulp fiber layer is moistened and light pressure is applied to form a densified paper-like skin which promotes wicking. A moisture-impermeable backing is then placed over the wood pulp layer and the product is laminated in the margins as before to provide a diaper product.

The absorbent product of the present invention is a stable product which upon manufacture and subsequent use as a diaper product or a sanitary napkin product remains stable. The product does not tend to break apart. Furthermore, one of the problems of utilizing wood pulp fibers or other cellulosic material in an absorbent batt is the tendency for these wood pulp fibers to collapse after contact with liquid if any pressure is placed upon the absorbent batt. The present invention with its substantially resilient fibrous web tends to prevent collapse and thereby permits utilization of the full absorption capacity of the filler portions. Furthermore, when the superabsorbent swells, the gel which forms is substantially self-sustaining under pressure and, thus, retains its thickness in spite of pressure being placed thereon. As such the swollen web acts as a frame for the regions of wood pulp fibers or other filler and prevents the pressure from being placed on the wet-collapsible wood pulp fibers.

The apertures or openings containing the filler tend to readily accept and store liquid in an available form for the adjacent superabsorbent material to gradually absorb and hence make efficient use of the superabsorbent material present. The overall result is a drier product. Because the wood pulp fibers are placed in an environment substantially surrounded by a stable fibrous superstructure, there is no compaction or calendering needed to stabilize the filler. The advantage of this is that there is no loss of the storage potential of the filler portion of the absorbent product. Another advantage is that the overall absorbent product is strong so that continuity is not interrupted when the product is placed under stress.

The cooperative action of the fibrous superstructure containing superabsorbent and the filler portions of the absorbent product provides an almost ideal environment for the reception and retention of liquid such as urine.

From the foregoing it would be observed that numerous variations and modifications may be effected without departing from the true spirit and scope of the novel concept of this invention.

What is claimed is:

1. An absorbent product comprising a fibrous superstructure comprising from about 10 percent to about 80 percent by weight of resilient fibers and from about 20 percent to about 90 percent by weight superabsorbent, said superstructure having apertures with one dimension at least about 0.25 inch, and a lightly compacted hydrophilic porous material covering at least one side of said superstructure said covering material providing a capillary pressure to absorbed liquid that is higher than the superstructure.

2. An absorbent product in accordance with claim 1 wherein said superstructure is a fibrous web of wet and dry resilient fibers.

3. An absorbent structure in accordance with claim 2 wherein said fibrous web is a non-woven web.

4. An absorbent product in accordance with claim 3 wherein said non-woven web is a polyester web.

5. An absorbent product in accordance with claim 1 wherein said hydrophilic porous material is selected from the group consisting of open-cell foam, styrofoam beads, cellulosic fibers, peat moss, acrylic fibers and mixtures thereof.

6. An absorbent product in accordance with claim 5 wherein said cellulosic fibers are wood pulp fibers, cotton linters, rayon fibers, or mixtures thereof.

7. An absorbent structure in accordance with claim 1 wherein said superabsorbent is present in an amount of at least about 200% by weight.

8. An absorbent product in accordance with claim 1 containing a wicking layer on at least one side of said superstructure.

9. An absorbent product in accordance with claim 8 wherein said wicking layer is a layer of tissue.

10. An absorbent structure in accordance with claim 8 wherein said wicking layer is a layer of compressed wood pulp fibers.

11. A disposable diaper comprising a moisture-impermeable backing and a moisture-permeable facing, said backing and said facing having sandwiched therebetween an absorbent product of a substantially stable, flexible, absorbent fibrous superstructure of resilient fibers containing at least about 20% by weight of superabsorbent and having openings and a layer of a hydrophilic porous material covering at least one side of said superstructure, said layer providing a capillary pressure to absorbed liquid higher than that provided by said superstructure.

12. A sanitary napkin comprising an absorbent product partially encompassed by a liquid barrier, said absorbent product comprising a substantially stable, flexible, absorbent, fibrous superstructure of resilient fibers containing at least about 20% by weight of superabsorbent and having openings and a layer of a hydrophilic porous material covering at least one side of said superstructure, said layer providing a capillary pressure to absorbed liquid higher than that provided by said superstructure.

* * * * *